(12) United States Patent
Lai

(10) Patent No.: US 6,256,366 B1
(45) Date of Patent: Jul. 3, 2001

(54) APPARATUS AND METHOD FOR RECONSTRUCTION OF VOLUMETRIC IMAGES IN A COMPUTED TOMOGRAPHY SYSTEM USING SEMENTATION OF SLICES

(75) Inventor: Ching-Ming Lai, Wakefield, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 09/435,269

(22) Filed: Nov. 5, 1999

Related U.S. Application Data

(63) Continuation-in-part of application No. 09/374,679, filed on Aug. 16, 1999, now Pat. No. 6,201,849, which is a continuation-in-part of application No. 09/375,347, filed on Aug. 16, 1999.
(60) Provisional application No. 60/144,987, filed on Jul. 22, 1999.

(51) Int. Cl.[7] .................................................. A61B 6/03
(52) U.S. Cl. ................................. 378/4; 378/17; 378/901
(58) Field of Search ..................................... 378/4, 15, 17, 378/901

(56) References Cited

U.S. PATENT DOCUMENTS

| | | | |
|---|---|---|---|
| 5,377,250 | * 12/1994 | Hu | 378/15 |
| 5,430,783 | * 7/1995 | Hu et al. | 378/15 |
| 5,802,134 | 9/1998 | Larson et al. | 378/4 |
| 5,909,477 | * 6/1999 | Crawford et al. | 378/4 |

OTHER PUBLICATIONS

Feldkamp, L. A., et al., "Practical Cone–Beam Algorithm", J. Opt. Soc. Am. vol. 1, No. 6, Jun. 1984, pp. 612–619.
Yan, X., et al., "Cone–Beam Tomography With Circular, Elliptical And Spiral Orbits", Phys. Med. Biol. vol. 37, No. 3, Nov. 1991, pp. 493–506.
Schaller, S., et al., "New Efficient Fourier–Reconstruction Method For Approximate Image Reconstruction In Spiral Cone–Beam CT At Small Cone Angles", SPIE, vol. 3032, Feb. 1997, pp. 213–225.
Wang, G., et al., "A General Cone Beam Algorithm", IEEE, vol. 12, Sep. 1993, pp. 486–496.
Kudo, H., et al., "Helicl–Scan Computed Tomography Using Cone–Beam Projections", Journal of Electronics, Information, and Communication Society, J74–D–II, 1991, pp. 1108–1114.

* cited by examiner

Primary Examiner—David V. Bruce
(74) Attorney, Agent, or Firm—McDermott, Will & Emery

(57) ABSTRACT

A system for reconstructing image data for a region includes a radiation source and an array of detectors located on opposed sides of the region used to generate scan data for the region from a plurality of diverging radiation beams, i.e., a cone beam. One or more image slices are defined for the region. Each image slice is partitioned into a plurality of image slice segments, and image data are generated for each segment. The image data for the segments are combined to generate image data for the slice.

26 Claims, 12 Drawing Sheets

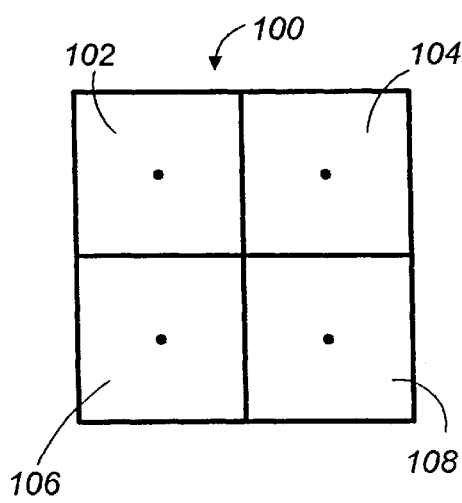
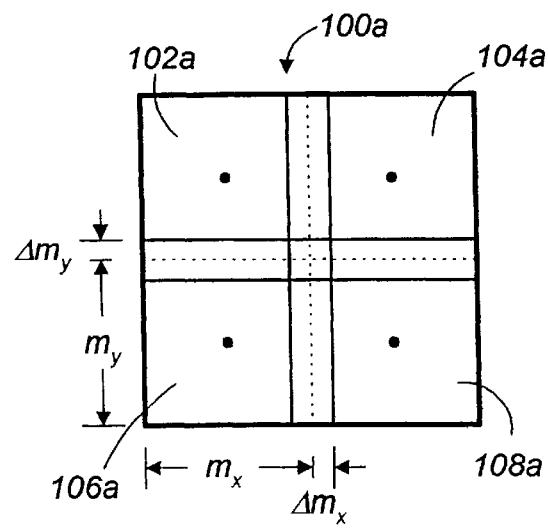
FIG. 12A  FIG. 12B
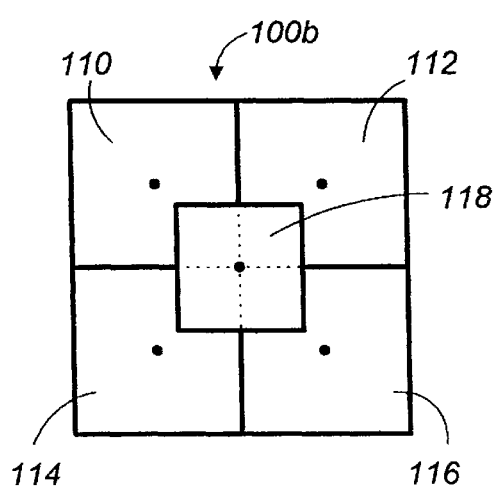
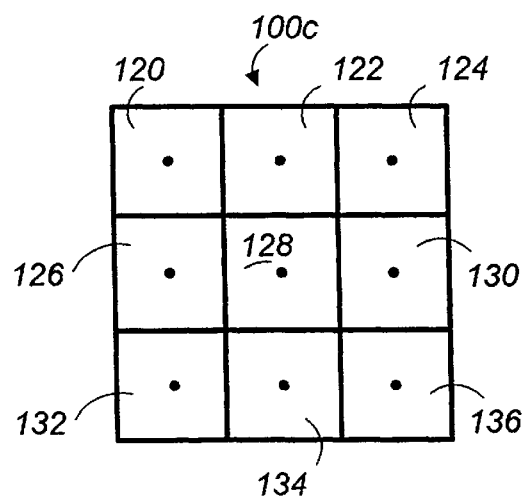
FIG. 12C  FIG. 12D

APPARATUS AND METHOD FOR RECONSTRUCTION OF VOLUMETRIC IMAGES IN A COMPUTED TOMOGRAPHY SYSTEM USING SEMENTATION OF SLICES

RELATION APPLICATIONS

This application is a continuation in part of U.S. application Ser. Nos. 09/374,679 now U.S. Pat. No. 6,201,849 issued Mar. 3, 2001 and 09/375,347, both filed on Aug. 16, 1999 and both incorporated herein in their entirety by reference. This application is also based on U.S. provisional application Ser. No. 60/144,987 filed on Jul. 22, 1999.

FIELD OF THE INVENTION

The present invention relates generally to computed tomography (CT) imaging and more particularly to three-dimensional CT imaging with improved efficiency and reduced image artifacts.

BACKGROUND OF THE INVENTION

FIG. 1 is a schematic axial view of a conventional third generation CT scanner 10 which includes an x-ray source 12 and an x-ray detector system 14 secured to diametrically opposite sides of an annular shaped disk 16. The disk 16 is rotatably mounted within a gantry support A (not shown), so that during a scan the disk 16 continuously rotates about a longitudinal z-axis 2( while x-rays pass from the source 12 through an object, such as a patient 20, positioned on a patient table 56 within the opening of the disk 16. The z-axis is normal to the plane of the page in FIG. 1 and intersects the scanning plane at the mechanical center of rotation 18 of the disk 16. The mechanical center of rotation 18 of the disk corresponds to the "isocenter" of the reconstructed image.

In one conventional system, the detector system 14 includes an array of individual detectors 22 disposed in a single row in a shape of an arc having a center of curvature at the point 24, referred to as the "focal spot," where the radiation emanates from the x-ray source 12. The source 12 and array of detectors 22 are positioned so that the x-ray paths between the source and each detector all lie in a "scanning plane" that is normal to the z-axis. Since the x-ray paths originate from what is substantially a point source and extend at different angles to the detectors, the diverging x-ray paths form a "fan beam" 26 that is incident on the detector array 14 in the form of a one-dimensional linear projection. The x-rays incident on a single detector at a measuring interval during a scan are commonly referred to as a "ray," and each detector generates an output signal indicative of the intensity of its corresponding ray. The angle of a ray in space depends on the rotation angle of the disk and the location of the detector in the detector array. Since each ray is partially attenuated by all the mass in its path, the output signal generated by each detector is representative of the attenuation of all the mass disposed between that detector and the x-ray source, i.e., the attenuation of the mass lying in the detector's corresponding ray path. The x-ray intensity measured by each detector is converted by a logarithmic function to represent a line integral of the object's density, i.e., the projection value of the object along the x-ray path.

The output signals generated by the x-ray detectors are normally processed by a signal processing portion (not shown) of the CT system. The signal processing portion generally includes a data acquisition system (DAS) which filters the output signals generated by the x-ray detectors to improve their signal-to-noise ratio (SNR). The output signals generated by the DAS during a measuring interval are commonly referred to as a "projection," "projection profile," or "view" and the angular orientation of the disk 16, source 12 and detector system 14 corresponding to a particular projection profile is referred to as the "projection angle."

If the detector array consists of N detectors, then N projection values are collected at each rotation angle. With the rays in a fan shape, these N projection values are collectively called a fan-beam projection profile of the object. The data of fan-beam projection profiles are often reordered or rebinned to become parallel-beam projection profiles. All rays in a parallel-beam profile have the same angle, called the parallel-beam projection view angle φ. The image of the object can be reconstructed from parallel-beam projection profiles over a view angle range of 180°.

During a scan, the disk 16 rotates smoothly and continuously around the object being scanned, allowing the scanner 10 to generate a set of projections at a corresponding set of projection angles. In a conventional scan, the patient remains at the constant z-axis position during the scan. When obtaining multiple scans, the patient or the gantry is stepped along the longitudinal z-axis between scans. These processes are commonly referred to as "step-and-shoot" scanning or "constant-z-axis" (CZA) scanning. Using well-known algorithms, such as the inverse Radon transform, a tomogram may be generated from a set of projections that all share the same scanning plane normal to the z-axis. This common scanning plane is typically referred to as the "slice plane."

A tomogram is a representation of the density of a two-dimensional slice along the slice plane of the object being scanned. The process of generating a tomogram from the projections is commonly referred to as "reconstruction," since the tomogram may be thought of as being reconstructed from the projection data. The reconstruction process can include several steps including reordering to form parallel-beam data from the fan-beam data, convolution to deblur the data, and back projection in which image data for each image pixel is generated from the projection data. In CZA scanning, for a particular image slice, all the projections share a common scanning plane, so these projections may be applied directly for convolution and to the back projector for generation of a tomogram.

The step-and-shoot CZA scanning approach can be a slow process. During this time consuming approach, the patient can be exposed to high amounts of x-ray radiation. Also, as the scanning table is moved between each scan, patient motion can result, causing motion and misregistration artifacts which result in reduced image quality.

Several approaches have been developed to decrease the time required to obtain a full scan of an object. One of these approaches is helical or spiral scanning in which either the object being scanned or the gantry supporting the x-ray source and detectors is translated along the z-axis, while the disk 16 with source 12 and linear detector array 14 are rotated about the patient. In helical scanning, the projections are normally acquired such that the z-axis position is linearly related to the view angle. This form of helical scanning is commonly referred to as constant-speed-helical (CSH) scanning.

FIG. 2A illustrates the data collected during a conventional CZA scan, and FIG. 2B illustrates the data collected during a CSH scan. As shown in FIG. 2A, if the x-ray source 12 and the detector system 14 are rotated about the object 20 while the object remains at a fixed z-axis location the scanning planes associated with all the projections collected by the detector system 14 will all lie in a common slice plane 50. As shown in FIG. 2B, if the object 20 or gantry is continuously translated in the direction of the z-axis while the disk is rotated about the object 20, none of the scanning planes will be coplanar. Rather, the scanning plane associated with each projection will lie at a unique position along the z-axis at a locus point on a helical set of loci.

FIG. 2B illustrates the z-axis coordinate of the scanning planes corresponding to helical projection angles in the interval (0, 10π).

In CZA scanning, all the projections share a common scanning plane, so these projections may be applied to the back projector after convolution to generate a tomogram. In CSH scanning however, each projection has a unique scanning plane located at a unique z-axis coordinate, so CSH projections may not be applied to a back projector. However, the data collected during a CSH scan can be interpolated in various fashions to generate a set of interpolated projections that do all share a common scanning plane extending normal to the z-axis. Each interpolated projection, for example, may be generated by combining two projections taken at equivalent projection angles and at different z-axis positions. These interpolated projections may be treated as CZA data and applied after convolution to a back projector to generate a tomogram.

CSH scanning requires some form of interpolation to generate a tomogram, and tomograms generated by CSH scanning therefore tend to be characterized by image artifacts. Also, since the CSH scan projection data, which are collected over an interval of z-axis locations, are combined to generate the interpolated CZA scan data, tomograms generated during CSH scanning have a wider effective slice plane width and, therefore, lower z-axis resolution, than tomograms generated by CZA scanning. However, helical scanning advantageously permits rapid scanning of a large volume of a patient. For example, in a time interval short enough to permit a patient comfortably to hold his or her breath (and thereby remain relatively motionless), a helical scan can collect enough data to fully scan an entire organ such as a kidney.

Another approach to decreasing scan time over CZA scanning is commonly referred to as "cone-beam scanning," in which a three-dimensional volume of the object or patient is scanned at once. In cone-beam scanning, the detection system includes a two-dimensional array of detectors instead of the one-dimensional array used in conventional scanning. The x-ray output from the source diverges in two dimensions to produce the equivalent of multiple fan beams, referred to as a "cone beam," along the z-axis dimension which illuminate multiple rows of plural detectors and therefore form a two-dimensional projection on the array.

In one form of a cone-beam system, the patient or object is maintained in a stationary z-axis position while the source and two-dimensional detector array are rotated around the patient or object. The patient is then moved to a new z-axis position, and the scan is repeated. In this type of step-and-shoot or "stationary cone beam" system, rather than sweeping out a plane, a volume of the object is scanned. After one volume is scanned, the source and detector are stepped along the z-axis to scan the next volume. Still another approach used to decrease scan time is helical cone-beam (HCB) scanning, in which a cone-beam configuration, i.e., a source and two-dimensional detector array, are rotated around the patient while the patient or gantry is continuously translated in the z-direction.

One approach to reconstructing volumetric image data is to divide it into a stack of slices. Standard two-dimensional reconstruction techniques, such as 2D filtered back projection (FBP), are used to reconstruct CZA and interpolated CSH data in non-cone-beam systems. FBP requires that the set of projections used for reconstruction of slices lie in the same plane. This condition is satisfied in CZA scanning, and interpolation is used in CSH scanning to produce a set of interpolated or simulated linear projections which effectively meet this requirement. In either case, 2D FBP is an efficient means of producing image data from the 1D fan beam projection data.

In cone-beam geometry, the required condition is only satisfied for a detector row coplanar with the source in a plane perpendicular to the z-axis, i.e., the center detector row. An image data slice perpendicular to the z-axis will be referred to herein as a normal slice. Other slices, i.e., slices which form a non-perpendicular angle with the z-axis, are referred to herein as oblique slices or tilted slices. In cone-beam CT, a 1D projection defined by the source and a given detector row will intersect a different slice in the object as the gantry rotates. For a helical cone beam scan, no slice is coplanar with the rays in all view angles. Conventional 2D FBP can be used to reconstruct cone-beam data by treating each row as an independent 1D projection. This approximation ignores the cone-beam geometry and results in image artifacts such as streaks and miscalculation of the reconstructed density.

The approximation can be improved by selecting certain oblique slices for the 2D reconstruction. One such approach is described in U.S. Pat. No. 5,802,134, entitled "Nutating Slice CT Image Reconstruction Apparatus and Method," of the same assignee as the present application. The contents of that patent are incorporated herein in their entirety by reference. In the approach described in the '134 patent, a 2D fan-beam projection profile can be interpolated from the cone-beam data for each slice at each rotation angle. The slice can be reconstructed from the fan-beam projection profiles over sufficient number of rotation angles. In this prior method, the projection profiles are interpolated directly from the actual cone-beam data. The mathematical relation between the interpolated rays of a projection profile and the original rays are complex. Because of this complexity, the prior method included a procedure based on computer simulation of scanning the oblique slice to determine the locations of interpolating rays. The result of the simulation depends on the accuracy of simulation.

Another approach to reconstruction using oblique slices is described in copending U.S. patent application Ser. No. 09/375,347 filed on Aug. 16, 1999, incorporated herein by reference.

An approximate method used to reconstruct cone-beam data is known as the Feldkamp algorithm and is described in L. A. Feldkamp, et al., "Practical cone-beam algorithm," *J. Opt. Soc. Am. I*, pp. 612–619, (1984).

In the Feldkamp algorithm, the rays are back projected in the three-dimensional cone. Algorithms such as Feldkamp, which attempt to incorporate the true cone-beam geometry of the data, are referred to as three-dimensional filtered back projection (3D-FBP) algorithms. Threedimensional algorithms reconstructing HCB data have also been developed. Examples of these algorithms are described in the following papers.

1. H. Kudo and T. Saito, "Three-dimensional helical-scan computed tomography using cone-beam projections," *Journal of Electronics, Information, and Communication Society*, J74-D-II, 1108–1114, (1991).

2. D. X. Yan and R. Leahy, "Cone-beam tomography with circular, elliptical and spiral orbits," *Phys. Med. Biol.* 37, 493–506, (1992).
3. S. Schaller, T. Flohr and P. Steffen, "New efficient Fourier reconstruction method for approximate image reconstruction in spiral cone-beam, CT at small cone angles," *SPIE International Symposium on Medical Imaging*, February, 1997.
4. G. Wang, T-H Lin, P. Cheng and D. M. Shinozaki, "a general cone beam algorithm," *IEEE Trans. Med. Imag.* 12, 486–496, (1993).

In all of these prior approaches to generating CT image slices, it is typical that each slice is characterized by a single point or small region near the center of the slice at which the image is at its highest quality. This point will be referred to herein as a "focal point" or "focus point" or "focusing point." As the distance from this point becomes greater, the quality of the image of the slice decreases.

SUMMARY OF THE INVENTION

The present invention is directed to an approach to improving the image quality over an entire slice which involves partitioning a slice into multiple segments and then generating data for each individual segment. The invention is directed to a method and apparatus for reconstructing image data for a region having a longitudinal axis. A radiation source and an array of detectors are located on opposed sides of the region. The radiation source emits radiation toward the array of detectors. At least one of the radiation source and the array of detectors is rotatable about the longitudinal axis through a plurality of projection angles to scan the region to generate scan data for the region. At least one image slice for the region is defined. The image slice is partitioned into a plurality of image slice segments, each of which has its own individual focus point. The image data for the plurality of image slice segments is combined to generate image data for the entire image slice.

In one embodiment, the array of detectors is a two-dimensional array of detectors. In this embodiment, the plurality of diverging radiation beams form a cone-beam of radiation. In this embodiment, the invention is applicable to scan data acquired by helical cone beam scanning.

In one embodiment, the at least one image slice is an oblique image slice which is oblique with respect to the longitudinal axis. An angle formed by the oblique image slice and the longitudinal axis is selected such that the image slice is coplanar with the radiation source for at least one projection angle. In particular, in one embodiment, the angle of the oblique slice is selected such that the slice is coplanar with the radiation source for three projection angles. Specifically, the image slice can be selected such that it is coplanar with the radiation source at projection angles of 0°, 90° and 180°.

In one embodiment, the image slice is partitioned such that at least two segments of the slice overlap. Preferably, the partitioning is performed such that all adjacent slices exhibit some degree of overlap. The overlap is used to smooth the data at the boundaries of segments such that discontinuities and/or artifacts at the boundaries are substantially reduced or eliminated.

The approach of the invention provides advantages over prior approaches. Each segment used to generate the data for the entire slice has its own individual focusing point. The image quality at each focusing point is relatively high compared to the rest of the segment. Since each individual segment has these high-quality portions, when the segments are combined, the overall composite slice has greatly improved image quality.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 12A–12D are schematic illustrations of possible slice partitioning configurations in accordance with the invention.

DETAILED DESCRIPTION OF PREFERRED EMBODIMENTS OF THE INVENTION

Figure 1:
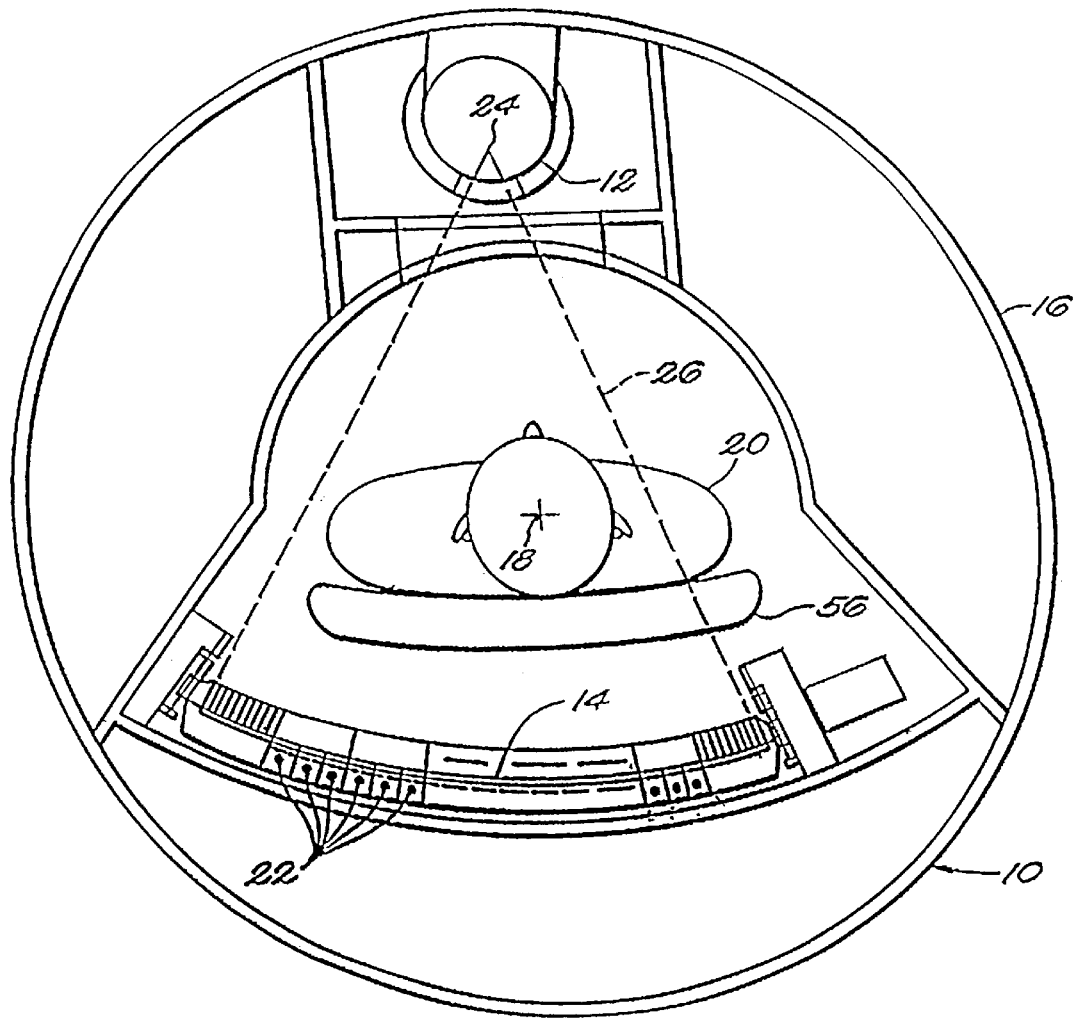
FIG. 1. is a schematic axial view of a typical computed tomography (CT) scanning system.
Figure 2A:
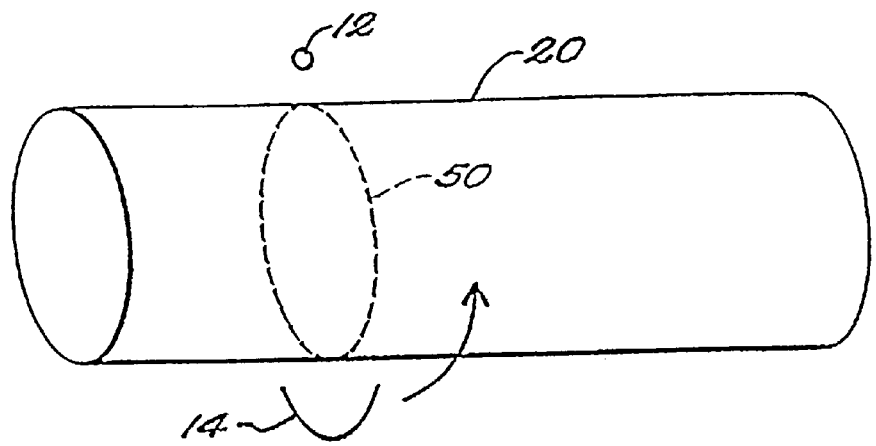
FIG. 2A illustrates the scanning path for a constant z-axis (CZA) scanning mode in a CT scanning system.
Figure 2B:
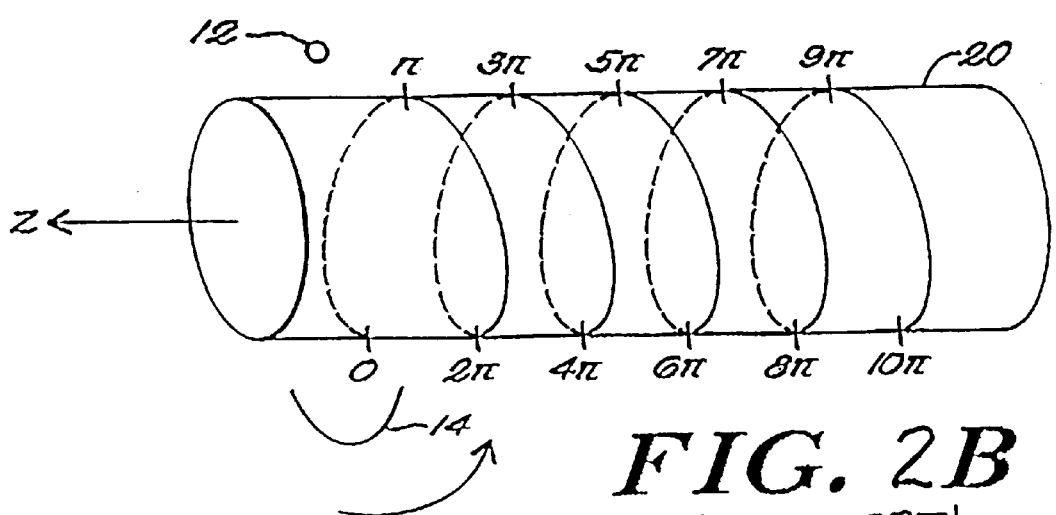
FIG. 2B illustrates the scanning path for constant-speed-helical (CSH) scanning in a CT scanning system.

In accordance with one embodiment of the present invention, a stack of oblique slices is selected for reconstruction. However, instead of generating the image of each slice by 2D reconstruction as in prior methods including the approach described in copending U.S. application Ser. No. 09/375,347 incorporated herein by reference, in accordance with the present invention, each slice is partitioned into multiple segments. At each view angle, the projection profile is interpolated to the rays most coincident with the segment. The image of each segment is reconstructed from such projection profiles optimally interpolated to that segment. The images from these multiple segments are then composed to form the image of the slice.

With the exception of the segment at the center of the slice, the image of each segment is more accurate than the image reconstructed by the prior methods in the same region of the segment. In one embodiment, this new method provides an improved reconstruction of volumetric images for a cone-beam system. The amount of improvement depends on the number of segments partitioned for the reconstruction.

In a filtered backprojection reconstruction method, the computation is dominated by the backprojection operation. The division of a slice into multiple segments does not increase the total backprojection time if these segments are not overlapped. However, in practice, these segments are slightly overlapped and the backprojection increase slightly in proportional to the extent of overlapping.

Convolution time for each segment is on the same order as that for the whole slice. Thus, the total convolution time is in proportion to the number of segments being partitioned, and it is greater than the prior methods. However, the amount of computations for convolution is much smaller than backprojection. There is only a slight increase in the overall reconstruction time.

The present method can achieve, or even exceed, the accuracy of prior 3D volumetric reconstruction methods. Yet, the amount of computation in 2D backprojection of multiple segments in multiple slices is considerably smaller than 3D backprojection for these slices. Thus, the present method is much faster than the prior 3D volumetric reconstruction methods.

In prior methods, the oblique slice is selected to be as coplanar with the rays as possible for reconstruction. But, with non-zero cone angle, no slice is perfectly coplanar with the rays. In general, along each projection path of the slice, more than one ray intersects the slice. The projection value of the ray intersecting the middle region of the slice is considered the best approximation to the actual projection value of the slice. The projection profile of the slice at each view angle is therefore interpolated from the collected projection data at the rays intersecting the middle line of the slice as described in copending U.S. application Ser. No. 09/375,347.

When the image is reconstructed from such interpolated projection profiles, the image is most accurate and satisfactory in the central region of the slice. In fact, the image quality in the central region of the slice is nearly as good as the image of single-row detector system. However, the image quality gets progressively unsatisfactory for the regions away from the center. It is desirable to be able to reconstruct the outer regions of the slice as accurate as the central region. If that can be achieved, the overall quality of the image will be greatly improved and will approach the quality of an image reconstructed from data of single-row detector system.

The present method is based on the rationale that the image is accurate at the central region of the slice because the projection values of the rays intersecting the central region are used for the reconstruction. In general, these rays do not intersect the outer regions, and consequently the reconstructed image in an outer region is not good as in the central region. In other words, the reconstruction is focusing on the central region. The center of the slice in this case can be considered as the "focusing point" of the reconstruction. The outer regions are not as good because they are out of focus for the reconstruction. If the projection values of the rays intersecting an outer region are used for the reconstruction, the focusing point will be shifted to the outer region. In that case, the outer region will be most accurate in the image of the slice and as good as the central region reconstructed by the prior method.

Therefore, if multiple images are reconstructed from each slice and each is based on the projection profiles optimally interpolated to a small region, then an improved image can be obtained by taking the portion of accurate region from each image and concatenating them into a composite image. The composite image will have multiple accurate regions. The number of accurate regions needed depends on the size of the cone angle and the required accuracy. When a sufficient number of accurate regions are used, the composite image will be satisfactory throughout the entire image area.

Since only the accurate region in each image is taken for the composite image, it is not necessary to reconstruct the whole area of the image. Thus, the present method divides the whole slice into a number of segments. For each segment, the projection values of the rays intersecting the middle region of the segment are used for 2D reconstruction of the segment. Such interpolated projection profiles could be used to reconstruct the whole slice. But to save the computing time, only the image over the segment area is reconstructed.

When the images of these segments are concatenated into a composite image, there may be a slight discontinuity of the image intensity across the boundaries of adjacent segments. This is because the interpolated projection profiles are slightly different between adjacent segments. Thus, it is preferred to partitioned the whole slice into slightly overlapped segments. The image intensities in the overlapped region is then feathered from the images of adjacent segments to give gradual change from one segment to the other. The composite image will appear to be reconstructed as a whole slice and with accuracy in every region matching the central region of the prior method.

The various features of the invention will now be described in detail. In order for a slice to be coplanar with the rays in all view angles, the X-ray focal spot or source must lie on the plane of that slice at all view angles. However, no slice can meet that requirement in a helical scan with constant translation speed. Thus, in accordance with the present invention, instead of looking for a perfect coplanar slice, a slice most coplanar with the rays is selected for reconstruction. A stack of oblique slices at successive locations can be selected. If the interpolated projection profiles were perfectly coplanar with these slices, the images would be reconstructed as accurately as they would be in a conventional system with a single row of detectors.

Figure 3:
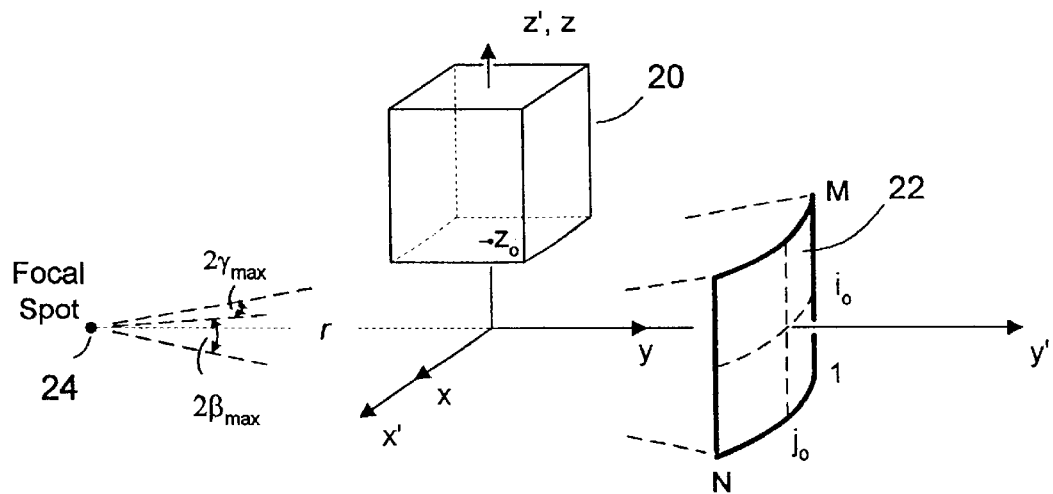
FIG. 3 is a schematic diagram which illustrates a scan object, the focal spot and detector array in a CT scanning system in accordance with the invention.
Figure 4:
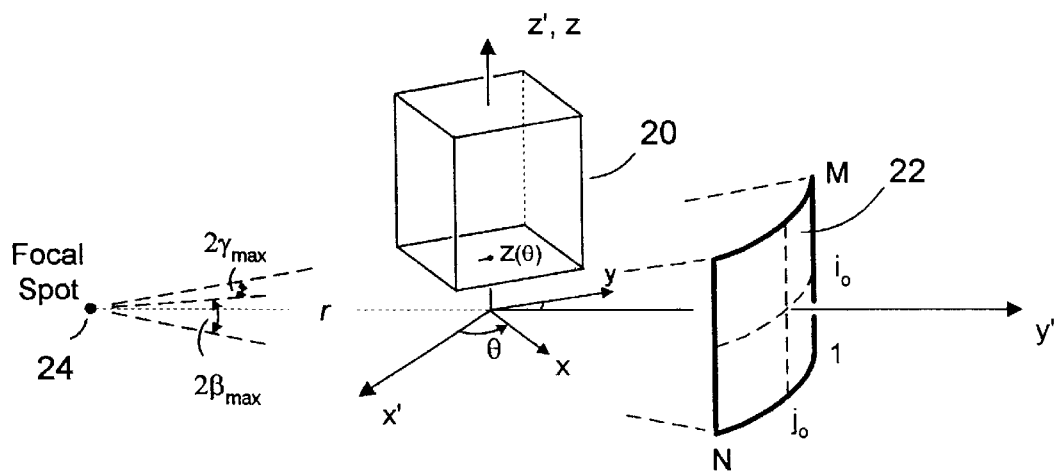
FIG. 4 is a schematic diagram which illustrates the system of FIG. 3 with 45 degrees of rotation.

FIG. 3 contains a schematic diagram illustrating a location and orientation of a scanning object 20 with respect to the focal spot 24 and the detector array 22 in a rotating frame at a starting rotation angle of θ=0, including a 3D matrix representing the image intensity of the scanning object 20. The focal spot 24 and the detector array 22 are fixed in a rotating frame defined by rectangular coordinates x'y'z', while the 3D matrix is referenced to a laboratory frame defined by rectangular coordinates xyz with the first slice located at $z=z_O$ Assuming, as seen in FIGS. 3 and 4, the rotating frame is rotating relative to the laboratory frame clockwise during a scan, the 3D matrix fixed relative to the laboratory frame is then rotating counterclockwise with respect to the rotating frame. During a helical scan, the 3D matrix is traveling at a constant speed along the −z direction with respect to the laboratory frame. The geometry of the 3D matrix at rotation angle of $\theta=45°$, for instance, is depicted in FIG. 4 as viewed in the rotating frame. The pitch of a helical scan is defined as the translation distance traveled by the object 20 relative to the laboratory frame during 360° rotation. If the pitch is 2p, the first slice of the 3D matrix is then located at $$z(\theta)=Z_o-p\,\theta/\pi \tag{1}$$

The detector array 22 includes M rows of detectors. For each row, there are N detectors, or channels. Detectors from the same channel of different rows constitute a column. Thus, the detector array can also be described as N columns of detectors. Usually, N is much greater than M. The N rays measured by each row of detectors will be referred to herein as a transverse fan, since they are radiated from the focal spot 24 and lie on a plane substantially transverse to the z-axis. The M rays measured by each column of detectors will be referred to as a longitudinal fan, since they are also radiated from the focal spot 24 but lie on a plane parallel to the z-axis. The fan angle of a transverse fan is $2\gamma_{max}$, in the order of about 60° as in a convention single-row detector system. The fan angle of a longitudinal fan is the cone angle $2\beta_{max}$, which is in the order of a few degrees. The cone beam system can be considered as having M transverse fans arranged in a small longitudinal fan angle and N longitudinal fans arranged in a large transverse fan angle.

Figure 5:
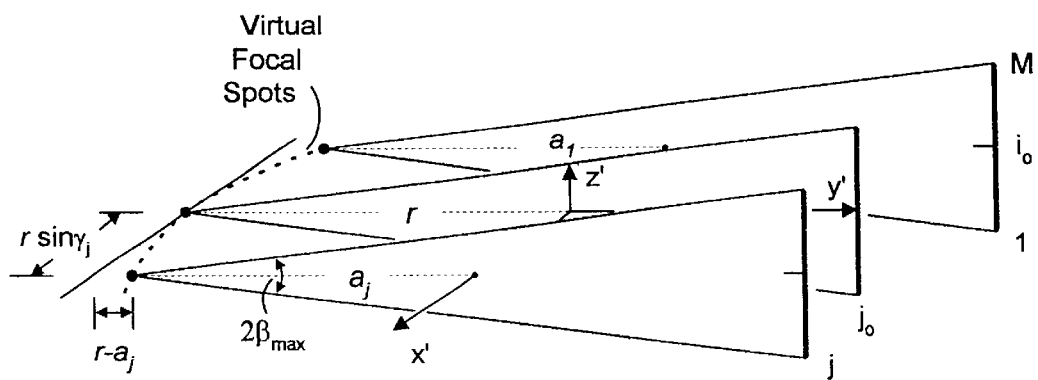
FIG. 5 is a schematic diagram which illustrates reordered rays consisting of N longitudinal fans in parallel, in accordance with the invention.

At each rotation angle, the data of a transverse fan comprises a fan-beam projection profile, as in a conventional single-row detector system. Each projection value in the projection profile is measured along the ray at an angle $\gamma_j$ relative to the ray of the central channel. It is preferable to reorder each fan-beam projection profile into a parallel-beam projection profile, as in parallel-beam reconstruction of 2D image for a single-row detector system. The reordering is performed on each row independent of the data in other rows. The reordered rays consist of N longitudinal fans in parallel, as shown in FIG. 5 for a step-and-shoot scan. In FIG. 5, the focal spot of the central fan is located at $y'=-r$, while the focal spot of a typical fan $j>j_0$ is located at $y'=-a_j$, with $a_j<r$. Each parallel longitudinal fan is a virtual fan mapped from an existing longitudinal fan in the actual cone-beam configuration. Thus, reordered rays contain N virtual focal spots and have a contour of a wedge shape.

Figure 6:
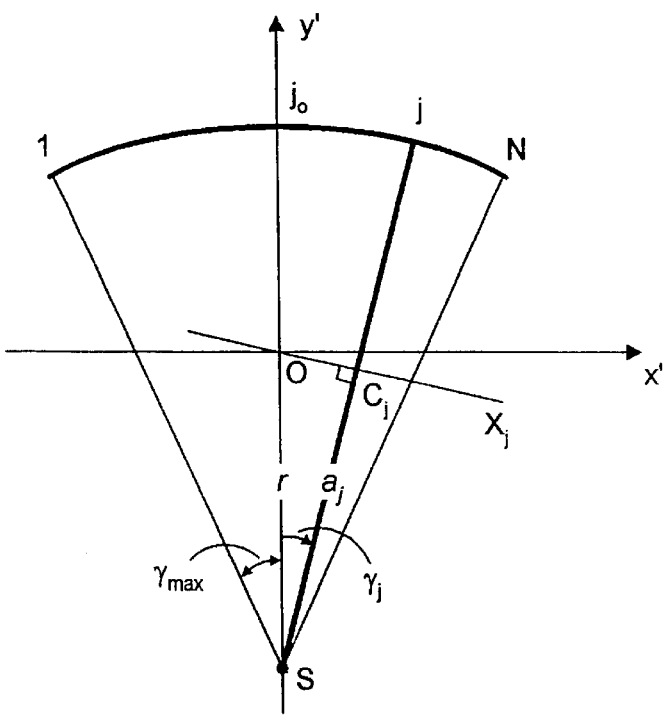
FIG. 6 is a detailed schematic illustration of a central transverse fan of FIG. 5, in accordance with the invention.

The exact location of a virtual longitudinal fan j with respect to the central longitudinal fan $j_o$ can be seen from the central transverse fan shown in FIG. 6, where each ray is the central ray of a longitudinal fan. In FIG. 6, the line $OX_j$ is normal to the longitudinal fan j with $C_j$ being the intersecting point, and it is mapped into the x'-axis of the reordered geometry in FIG. 5. The distance $a_j$ is the distance between the focal spot S and the point $C_j$, with $$a_j=r\,\cos\,\gamma_j=r\,\cos\,((j-j_o)\,\delta) \tag{2}$$

where $\delta$ is the angular spacing between adjacent detector channels which gives the angle $\gamma_j=(j-j_o)\,\delta$. The distance $OC_j$ is the distance between a longitudinal fan j and the central longitudinal fan $j_o$. It is equal to $r\,\sin\gamma_j$, or $r\,\sin((j-j_o)\,\delta)$. Because the distance $a_j$ depends on j, the virtual focal spots in the reordered geometry are not lying on a straight line. Also, the virtual longitudinal fans are not located at equal interval along the x'-axis, as the result of nonlinear dependence of $OC_j$ on j.

Figure 7:
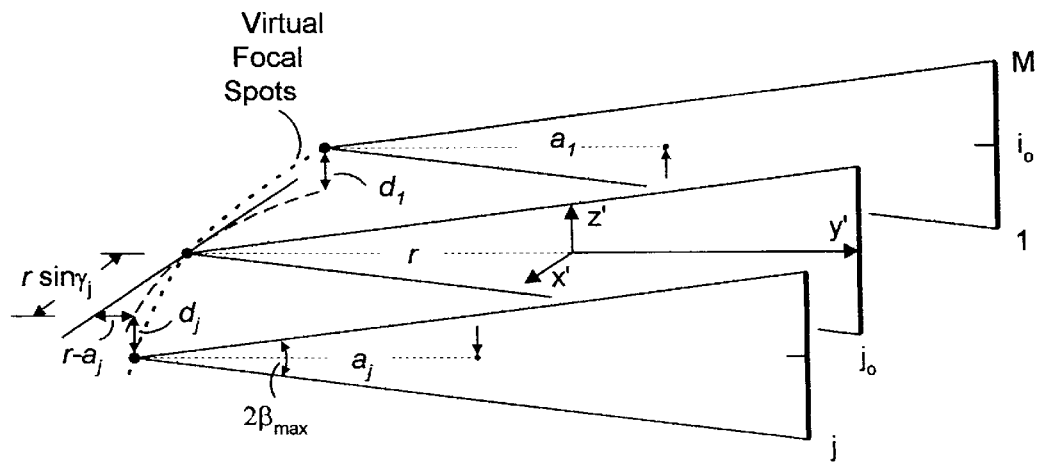
FIG. 7 is a schematic diagram of reordered rays from a helical scan illustrating slight distortion from wedge shape due to translation along the longitudinal axis.

The reordered rays of a helical scan are slightly distorted from the wedge shape, as shown in FIG. 7 at the view angle of $\phi=0°$. Unlike a step-and-shoot scan, the virtual longitudinal fans, while parallel, are no longer at the same z position. This is because the data of each virtual longitudinal fan are actually collected at a different time from the others. The central longitudinal fan (of column $j_o$) is the only one collected at rotation angle of $\theta=0°$. The first virtual longitudinal fan (of column j=1) is collected at a time ahead of rotation angle $\theta=0°$, and it is offset from the central fan in the +z direction. Similarly, the last virtual longitudinal fan (of column j=N) is collected at a time after the rotation angle $\theta=0°$, and therefore it is offset from the central fan in the −z direction. If the pitch of the helical scan is 2p, the offset for the virtual longitudinal fan j in z direction is given by $$d_j=-p\,\gamma_j/\pi=-p\,(j-j_o)\,\delta/\pi \tag{3}$$

Figure 8:
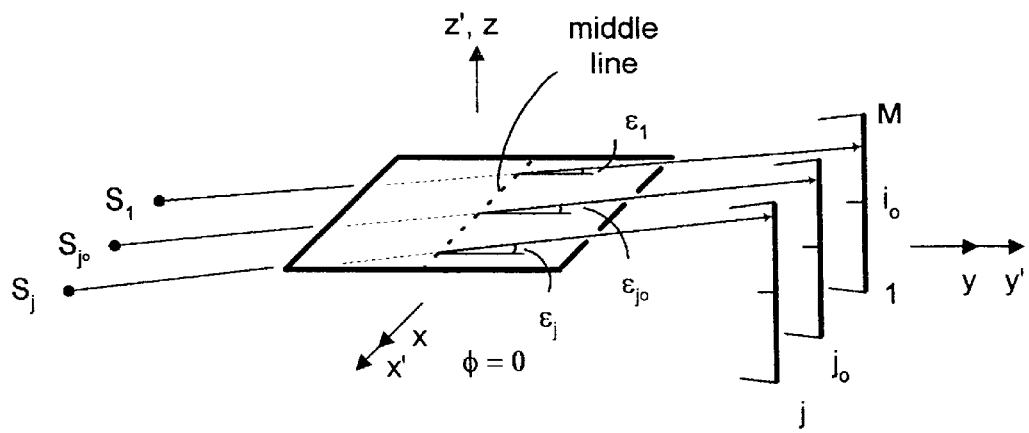
FIG. 8 is a schematic diagram illustrating aberration angles in a normal slice.

The line on the slice passing the z-axis and perpendicular to the longitudinal fans will be referred to as the middle line of the slice. Its orientation varies with the view angle. Suppose a normal slice is selected for reconstruction. The middle line of the slice is the line y=0 at a view angle of $\phi=0°$, as shown in FIG. 8. The angle between the slice and the ray intersecting the middle line is referred to as the aberration angle. It varies with the channel and the view angle. The aberration angle of channel j is illustrated in FIG. 8 as $\epsilon_j$.

Figure 9A:
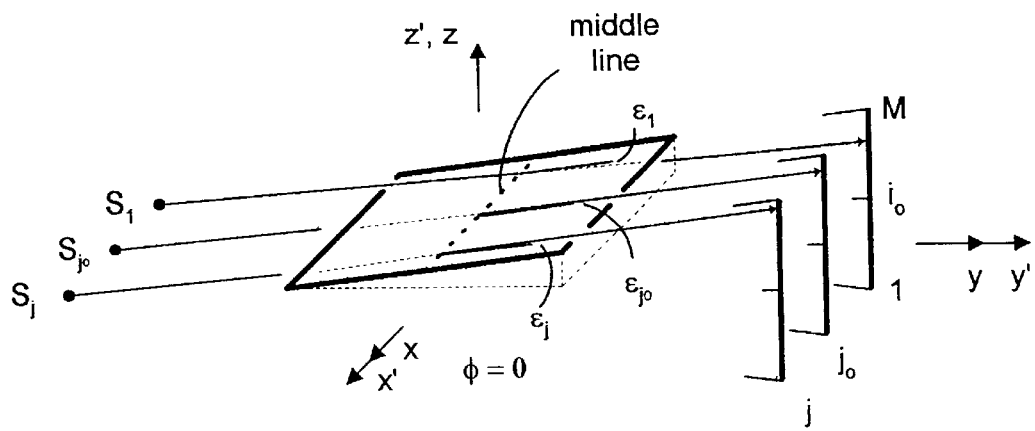
FIGS. 9A and 9B are schematic diagrams illustrating aberration angles in an oblique slice at view angles of 0 and 90 degrees, respectively.
Figure 9B:
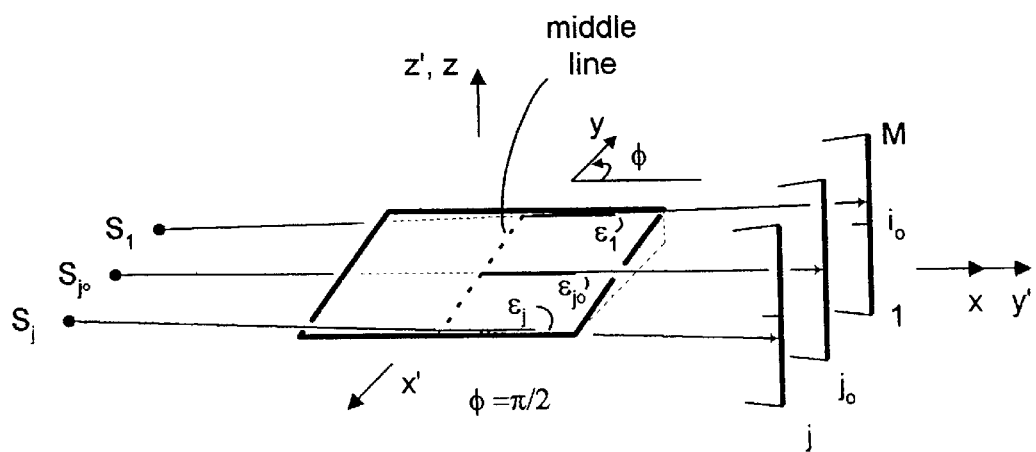

The magnitude of the aberration angles from all channels indicates the closeness of the slice being coplanar with the rays. The optimal slice for reconstruction is the one with the smallest aberration angles. An oblique slice can have smaller aberration angles than the normal slice. The aberration angle $\epsilon_j$ of an oblique slice is shown in FIG. 9A at view angle of $\phi=0°$, and in FIG. 9B at a view angle of $\phi=90°$. As shown in FIG. 9A, the aberration angles of an oblique slice at a view angle of $\phi=0°$ are less than those of a normal slice. As shown in FIG. 9B, the aberration angles of the oblique slice at a view angle of 90° are also smaller than those of the normal slice.

For ease of understanding of the description, reconstruction of only one oblique slice will be described. It will be understood that the description can be extended to any number of slices. Let (u,v) be a rectilinear coordinate on the slice with u-axis being the line intersected by the xy-plane. The oblique slice can be considered to be the result of rotating a normal slice about the u-axis for an angle $\alpha$. The angle $\alpha$ is the oblique angle of the slice.

Figure 10A:
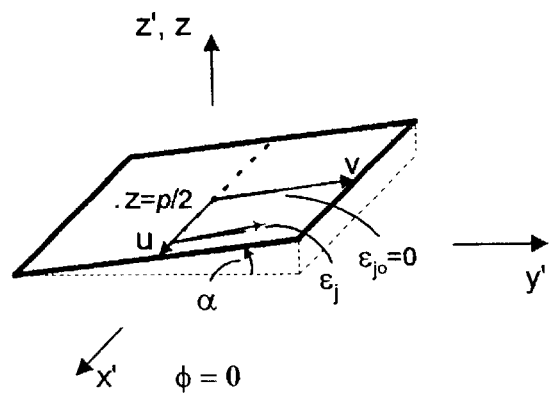
FIGS. 10A, 10B and 10C are schematic diagrams illustrating an oblique slice in I accordance with the invention at view angles of 0, 90 and 180 degrees, respectively.

An oblique slice in accordance with the invention at view angle of $\phi=0°$ is depicted in FIG. IOA, where the oblique angle $\alpha$ is the angle between v-axis and y'-axis. In one embodiment, it is preferred to select the oblique angle a such that the v-axis is coincident with a ray of the central longitudinal fan. In that case, the aberration angle of the central channel is zero, i.e., $\epsilon_{jo}=0$. The oblique slice is selected at a center location of p/2 with a slope of $\tan\alpha$ in the +y' direction. Because the z position of any other longitudinal fan is offset from the central longitudinal fan by $d_j$ given in Equation (3) in the reordered parallel-beam geometry, the aberration angles of other channels are non-zero. Nevertheless, they are small and get smaller as the channel is closer to the central channel. The aberration angle $\epsilon_j$ of a channel j far away from the central channel is depicted in FIG. 10A.

Figure 10B:
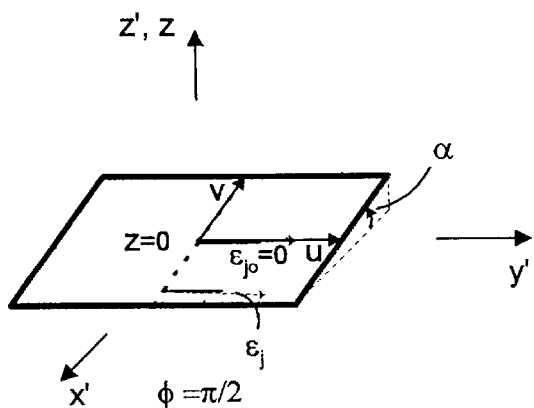

At a pitch of 2p for the helical scan, the oblique slice is preferably selected at a location 10 along the z axis with its center at z=p/2. Then, at a view angle of φ=π/2, the center of the slice will have traveled by p/2 to the location of the isocenter as shown in FIG. 10B. The oblique slice is traveled to z=0 with the slope tanα in the −x' direction. The u-axis becomes coincident with the central ray of the central longitudinal fan. Again, the aberration angle of the central channel is zero, $\epsilon_{j_o}=0$, while other channels $\epsilon_j \neq 0$.

Figure 10C:
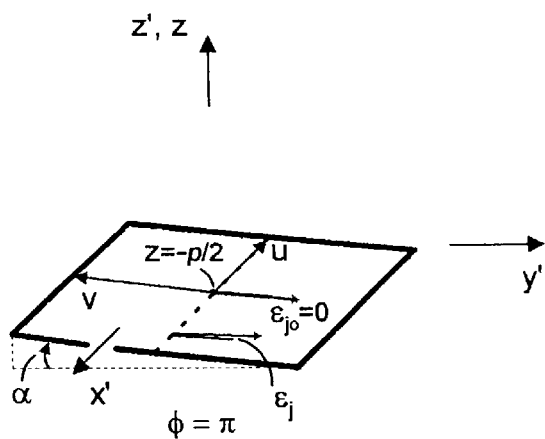

At a view angle of φ=π, the geometry of the oblique slice is as shown in FIG. 10C. Here, the v-axis becomes coincident with another ray of the central longitudinal fan and $\epsilon_{j_o}=0$. The oblique slice has traveled a distance p. The oblique slice is further traveled to z=−p/2 with the slope tanx in the −y' direction. For reconstructing the image from a half scan, the data at view angle φ=π is redundant with that at view angle φ=0. The figure is shown here for better demonstration of the oblique slice; in general the projection data of the oblique slice at φ=π are not needed.

It should be noted that when an oblique slice is coincident with a ray of the central longitudinal fan the focal spot is lying on the slice plane. In that case, the oblique slice will be coplanar with a transverse fan containing this ray. Therefore the oblique slice shown in FIG. 10A is coplanar with a transverse fan of the divergent cone-beam data a rotation angles of θ=0, π/2, and π.

It is not necessary to choose the oblique slice with exactly a null aberration angle at the central channel at φ=0, φ=π/2, and φ=π. Any oblique slice close to the oblique angle described here is acceptable. As can be seen from the figures, the oblique angle α is roughly equal to one half the cone angle, that is, $\alpha \approx \beta_{max}$. In fact, a is preferably less than $\beta_{max}$, because the pitch 2p is usually shorter than the z dimension of the detector array at the isocenter.

Figure 11:
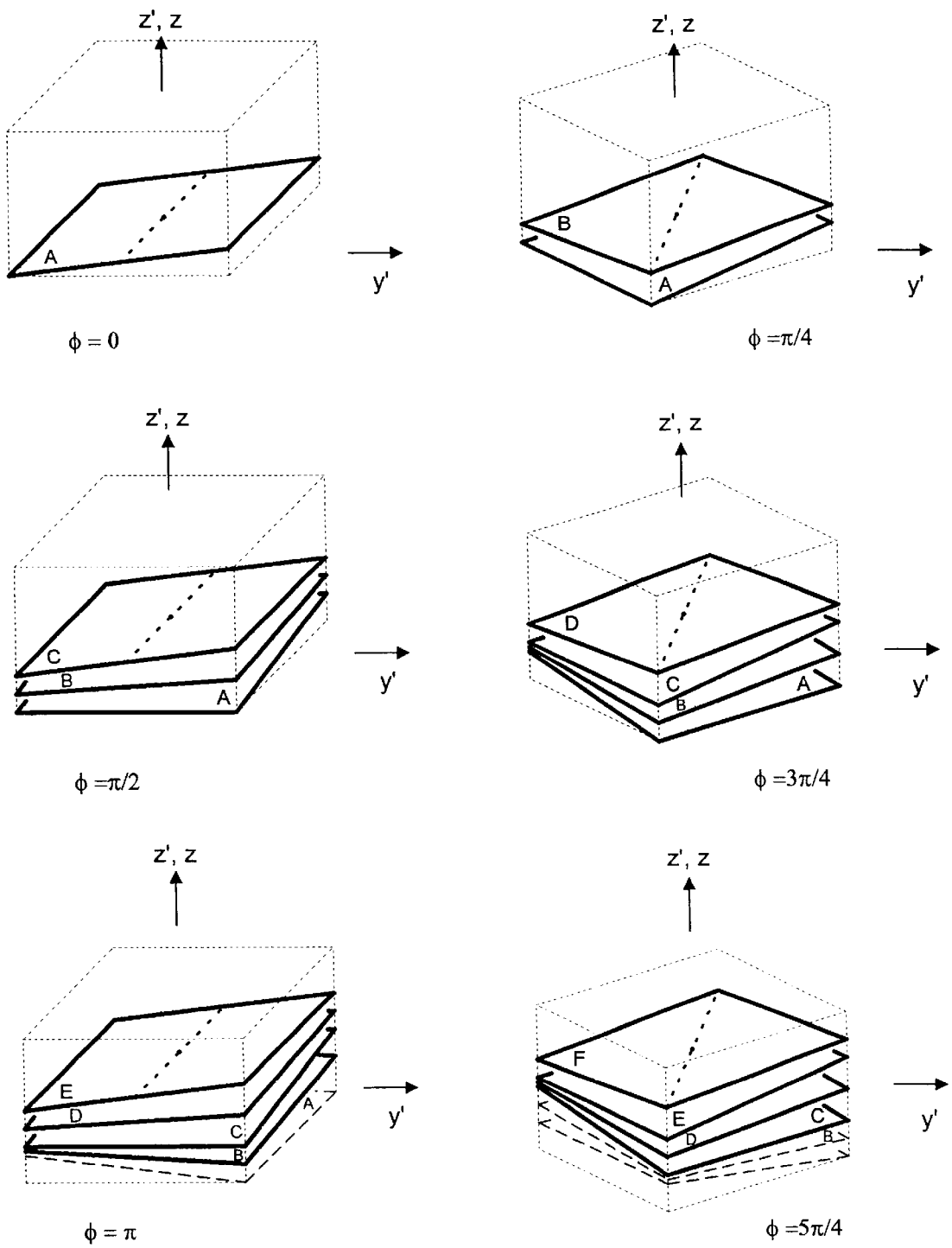
FIG. 11 schematically illustrates formation of a stack of oblique slices at multiple view angles in accordance with the invention.

In practice, multiple oblique slices at successive locations in the z direction are selected for reconstruction. As an example, assume four slices are selected over the length of p in the z dimension. Once a slice is selected, its projection profiles are interpolated from the reordered data over the next 180° view angles. At view angle φ=0, the first slice A is selected as illustrated in FIG. 10A and reproduced in FIG. 11. At view angle φ=π/4, the second slice B is selected as if it were at zero view angle as in FIG. 10A. In the meantime, the first slice has traveled for p/4 and oriented at an azimuth angle of 45° with respect to the rotating frame x'y'z, as shown in FIG. 11 for φ=π/4. Similarly, the third slice C and forth slice D are selected at view angle of φ=π/2 and φ=3π/4, respectively, as if they were at zero view angle. At view angle φ=π, the fifth slice E is selected, while the interpolation for the projection profiles of first slice A has been completed.

From there on, at every π/4 interval one new slice is selected and one slice has completed the π view angle range as shown in the instance φ=5π/4 of FIG. 11. Thus, there are four slices for the interpolation of projection profile at each view angle starting from φ=3π/4. These four slices are located over the length p in the z dimension.

In general, if m oblique slices are required for the interpolation at each view angle, the interval of view angle to select a new slice is π/m. Let $\Phi_k$ be the view angle where the k slice is first selected as if it were at zero view angle, we have $$\Phi_k = k \pi/m \quad (4)$$

with k=0, 1, 2, ..., $m_k$−1, and $m_k$ is the total number of slices to be selected over the whole length of the object. At the view angle of φ=π−π/m and thereafter, there will be m slices within the length p at each view angle. Given a view angle φ, these m slices are the slices with $\Phi_k$ in the range of φ−π<$\Phi_k$≤φ. They all have the same oblique angle α. However they are separated by a constant distance of p/m along the z-axis, and oriented at different azimuth angles of π/m apart.

When a slice is partitioned into more segments, a more accurate image of the slice can be obtained. However, the amount of projection data required for reconstructing a segment is the same as that required for reconstructing the whole slice. The only difference is the projection profiles interpolated for a segment from all view angles will be focused on the center of the segment rather than the center of the slice. Thus, the computing time of generating the projection profiles and the subsequent convolution operation is proportional to the number of segments. There is a tradeoff between image quality and computing time.

Depending on the cone angle of the scanner, the image area of interest, the image accuracy required, and other factors, the slice can be partitioned into segments in many different configurations. Four different configurations are shown in FIGS. 12A–12D for illustration and description. FIG. 12A illustrates a slice 100 partitioned into four segments 102, 104, 106, 108. In this example, the segments do not overlap with each other. As shown in FIG. 12B, it is preferred that the segments 102a, 104a, 106a, 108a of the slice 100a slightly overlap. A partition including five segments 110, 112, 114, 116, 118 is shown in FIG. 12C. In this configuration, the central segment 118 is completely overlapped with the other four segments 110, 112, 114, 116. The image intensity will be fully represented by the central segment 118 near the center of the slice 100b, with increasing averaging with one of the four segments as the pixel is located further away from the center of the slice 100b. Another configuration including nine segments is shown in FIG. 12D, where, for simplicity, the overlapped regions between adjacent segments are not shown.

In a partitioning configuration, the size of each segment and the extension for overlapping with adjacent segments is determined. A segment does not have to be the same size or same shape with other segments. The focusing point for reconstruction is also selected for each segment. The focusing point is the location where the image intensity is most accurate, and it does not have to be exactly at the center of the segment. The focusing points for the segments are marked as circular dots in FIGS. 12A–12D. In one embodiment, all slices have the same partitioning.

The image of a slice is stored in a matrix having dimensions $n_x$ by $n_y$. Each segment is a sub-matrix of this matrix. Suppose there are $n_s$ segments, and the dimension of the $l^{th}$ segment is $m_{xl}$ by $m_{yl}$. The focusing point is located at ($X_{okl}$, $Y_{okl}$), while the center of the segment is located at ($X_{ckl}$, $Y_{ckl}$). The focusing point of the $5^{th}$ segment in FIG. 12C, for example, is labeled as ($X_{ok5}$, $Y_{ok5}$). The z coordinate of the focusing points, $Z_{okl}$, are not shown here, since the figure is a two-dimensional view on the xy-plane.

Although a slice is partitioned into a number of segments, each segment is treated like a slice. The projection profiles of a segment are interpolated from the collected data like a whole slice, except the interpolation is optimized for the segment. In the reconstruction method using filtered backprojection, the interpolated projection profiles are convoluted with a kernel as in reconstruction of a whole slice. However, it is only necessary to back-project the convoluted projection profiles to a sub-matrix representing the segment.

In order to interpolate the projection profiles optimally for a segment, the interpolation of projection profiles for a slice in general are determined. At a view angle, the projection profile includes N channels with one projection value at each channel. If a slice were coplanar with the rays, then each channel of the projection profile would be defined by the projection value of a ray. However, with non-zero cone angle, no slice is coplanar with the rays. With the exception of a few channels in a few view angles, more than one ray intersects the slice in each channel. Therefore, a ray is selected to best approximate the projection path of the slice at each channel. The projection value of the selected ray is interpolated from the collected projection data as the projection value of the slice at that channel.

The ray selected for such interpolation intersects the slice at a point along the projection path. There will be N intersecting points, one for each channel of a projection profile. These N intersecting points are adjacent to each other and form a line on the slice, and they are substantially perpendicular to the rays. In the geometry of reordered projection data, with parallel rays on the transverse plane, the intersecting line is substantially a straight line.

In the method using oblique slices, described in copending U.S. application Ser. No. 09/375,347, incorporated herein by reference, the intersecting line was chosen to be the middle line of the slice, which passes the center of the slice at every view angle. In this manner, the interpolated projection profiles were focused on the center of the slices from all view angles. Consequently, the reconstruction image is most accurate at the center of the slice.

Therefore, in order to reconstruct an accurate image over the area of the segment, the projection profiles should be focusing on a point near the center of a segment. The intersecting line should be selected to pass the focusing point of the segment. This line will be referred to as the middle line of the segment. To interpolate for the projection profile according to the middle line of the segment, the geometry of the middle line in the rotating frame should be known at every view angle.

In the reordered parallel-beam geometry, the projection data $P_{ij}(\phi)$ can be considered as 10 consisting of N longitudinal fans, as shown in FIG. 7. The rays of longitudinal fan j lie on an y'z'-plane parallel to that of the central longitudinal fan $j_o$, but separated by a distance of $r \sin((j-j_o) \delta)$ in the x' direction. The longitudinal fan j is also offset from the central longitudinal fan $j_o$ by $d_j$ in z' direction and by $r-a_j$ in the y' direction, as described above. The middle line of a segment is perpendicular to the longitudinal fan j. It is parallel to the middle line of the slice and lying on the x'z'-plane with y'=0. Given the oblique angle $\alpha$ and the view angle $\phi$, the slope of the middle line on the x'z'-plane can be determined. Based on the slope, the z position of the segment middle line at channel j can be derived from the z position of the segment middle line at the central channel $j_o$, namely, the focusing point.

Firstly, since the oblique slices are separated by p/m and translating along the z-axis at the rate of distance p over view angle of π, the z position of the center of the slice can be written as $$Z_{kjo} = Z_o + k\, p/m - \phi p/\pi \qquad (5)$$

where $z_o$ is a constant representing the z position of the first slice at starting view angle of $\phi=0$, and k is the slice number with k=0, 1, 2, ..., $m_k$−1. Secondly, the slope of the segment middle line can be determined from the simple geometry of the oblique slice k when it was selected at $\phi=\Phi_k$. As can be seen from FIG. 10A and the $\phi=0$ diagram of FIG. 11, the slope of the oblique slice is tanα along the y' direction. Thus, the z' coordinate of the oblique slice at $\phi=\Phi_k$ can be written as $$Z'(\Phi_k) = Z_{kjo} + Y' \tan\alpha. \qquad (6)$$

The slice middle line is the line of y'=0 on the slice. The slice middle line at $\phi=\Phi_k$ has a constant coordinate of $z'=Z_{kjo}$, and the slice middle line is parallel to the x' axis as shown in FIG. 10A. The segment middle line is the line of $y'=y'_{okl}$ on the slice for the segment l.

Figure 13:
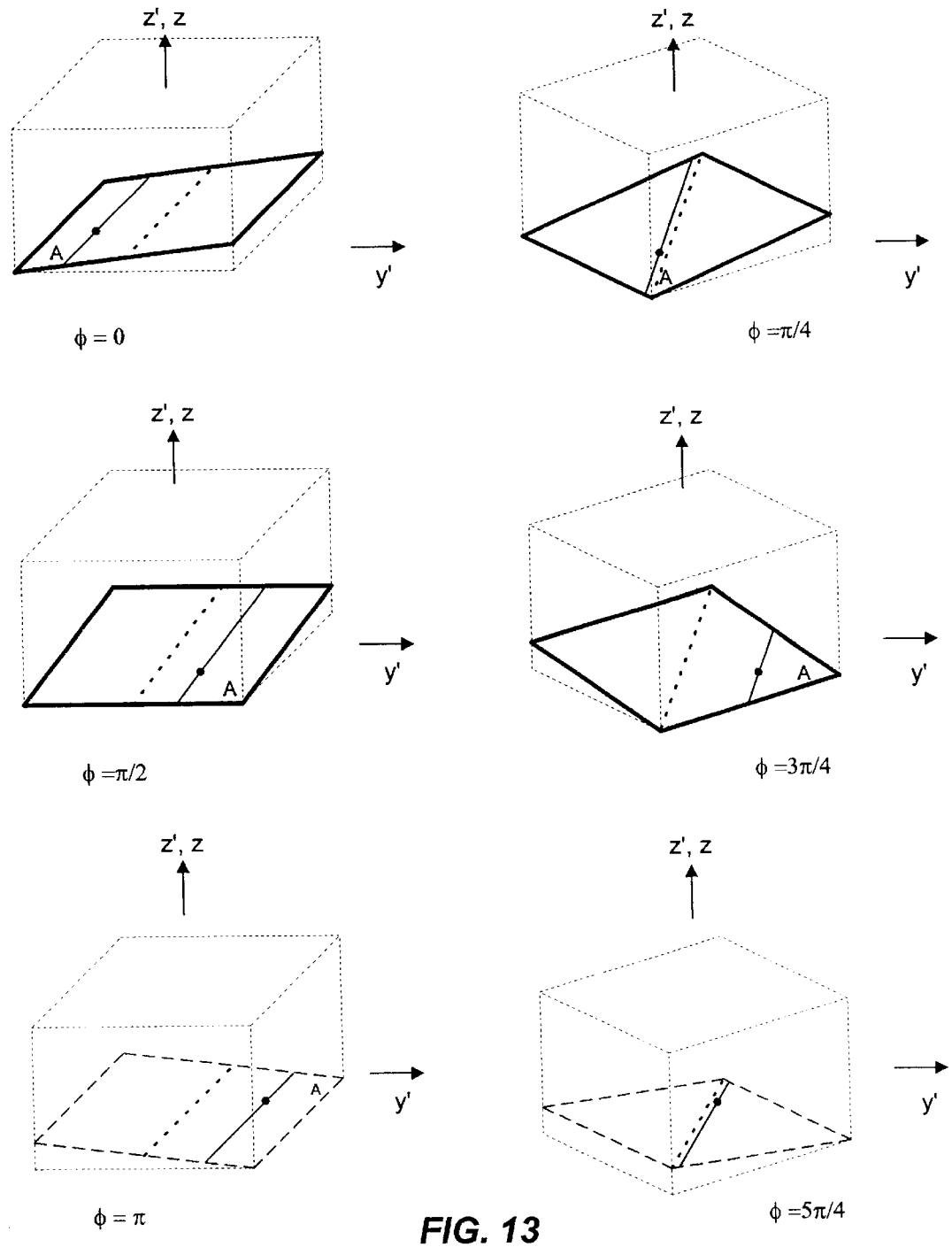
FIG. 13 contains schematic diagrams of a partitioned slice in accordance with the invention in a rotating frame at a series of rotation angles.

As an example, FIG. 13 contains a schematic illustration of rotation of the slice in a rotating frame through a series of rotation angles. The middle line of a segment is shown as a solid line in the $\phi=0$ diagram of FIG. 13, when slice A is first selected for interpolation. The segment middle line passes the focusing point shown as a circular dot and is parallel to the slice middle line, shown as a dashed line. In the rotating frame, the location of the focusing point and the orientation of this segment middle line are shown in the remaining diagrams of FIG. 13. The segment middle line remains in parallel with the slice middle line.

At a subsequent view angle of $\phi > \Phi_k$, the segment middle line can be located by rotating the oblique slice about the z'-axis for an angle of $\phi-\Phi_k$ and set the y' coordinate to $y'_{okl}$. When the oblique slice is rotated about the z'-axis for $\phi-\Phi_k$, the z' coordinate of the oblique slice becomes $$Z'(\phi) = Z_{kjo} - X' \tan\alpha \sin(\phi-\Phi_k) + y' \tan\alpha \cos(\phi-\Phi); \qquad (7)$$

and the y' coordinate of the focusing point becomes $$Y'_{okl} = Y_{okl} \cos(\phi-\Phi_k) - X_{okl} \sin(\phi-\Phi_k) \qquad (8)$$

The segment middle line is given by Equation (7) with $y'=Y'_{okl}$. In addition, we know that the x'coordinate of the segment middle line is $r \sin(j-j_o)\delta$ for channel j. Thus, by further setting $x'=r \sin(j-j_o)\delta$ to Equation (7), we have the z position of the segment middle line at channel j as $$Z_{klj}(100) = Z_{kjo} - r \tan\alpha \sin(\phi-\Phi_k) \sin((j-j_o)\delta) + Y_{okl} \tan\alpha \cos^2(\phi-\Phi_k) - X_{okl} \tan\alpha \sin(\phi-31\ \Phi_k) \cos(\phi-\Phi_k) \qquad (9)$$

for the oblique slice k at a view angle of $\phi > \Phi_k$. Using Equation (5) for $Z_{kjo}$, it becomes $$Z_{klj}(\phi) = Z_o + k\, p/m - \phi p/\pi - r \tan\alpha \sin(\phi-\Phi_k) \sin((j-j_o)\delta) + Y_{okl} \tan\alpha \cos^2(\phi-\Phi_k) - X_{okl} \tan\alpha \sin(\phi-\Phi_k) \cos(\phi-\Phi_k) \qquad (10)$$

This point of the segment middle line is intersected by the ray to be interpolated. Thus, $Z_{klj}(\phi)$ is also considered as the z position of the interpolated ray. In general, the z position of a ray interpolated from a longitudinal fan on y'z'-plane is defined by the z coordinate of the ray at $y'=y'_{okl}$.

Figure 14:
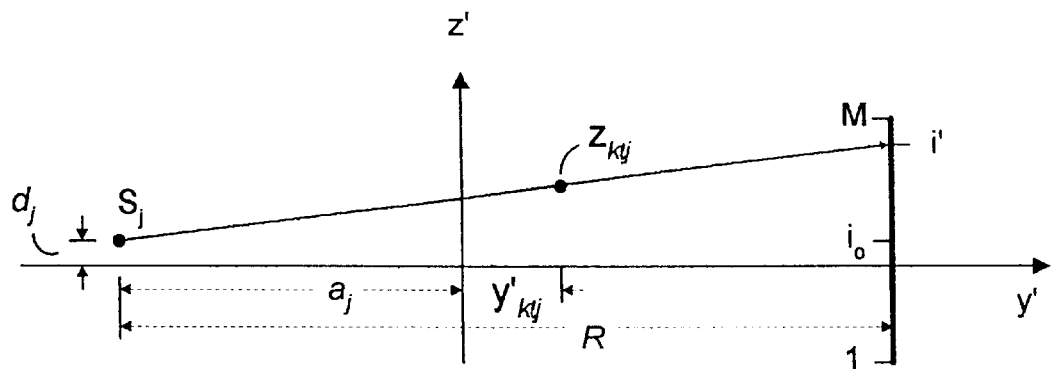
FIG. 14 schematically illustrates the geometry of a ray with respect to a longitudinal fan in accordance with the invention.

To interpolate a ray from the longitudinal fan, it should be noted that the oblique slice k is measured by the detector array for view angles between $\phi=\Phi_k$ and $\phi=\Phi_k+\pi$. Within that angular range, the corresponding detector row number of the ray intersecting the segment middle line is related to the z position $Z_{klj}(\phi)$ by $$i' = i_o + (Z_{klj} - d_j)\, R / (a_j + y'_{okl}) \qquad (11)$$

assuming $Z_{klj}$ and $d_j$ are measured in terms of the number of rows of detectors. The geometry of the ray with respect to the longitudinal fan j is shown in FIG. 14, where $i_o$ is the central row number and R is the distance from the focal spot $S_j$ to the column of M detectors. The value i' in Equation (11) is not an integer number. It can be written as the sum of a truncated integer q and a fractional part f $$i' = q + f \qquad (12)$$

with $0 \leq f < 1$. If a linear interpolation method is used to interpolate for the projections of the oblique slice, the interpolated projection value $P_{i,j}(\phi)$ for channel j will be calculated as $$P_{i,j}(\phi) = (1-f) P_{qj}(\phi) + f\, P_{q+1,j}(\phi) \qquad (13)$$

Although linear interpolation provides a method of obtaining the projection value $P_{i,j}(\phi)$, it is not the only possible choice for the interpolation. For example, if the slice width is greater than the height of one detector (length along the z-axis), the data can be oversampled in the z dimension. A resampling method, such as the approach described in a copending U.S. patent application Ser. No. 09/375,151, entitled, "An Improved Cone-Beam CT System With Oversampling Detector Array and Resampling Technique," by C. M. Lai, filed on Aug. 16, 1999, assigned to the same assignee as the present application (Attorney Docket No.: ANA-177), incorporated herein by reference, can be used to calculate for the projection value $P_{i,j}(\phi)$.

There are N projection values $P_{i,j}(\phi)$ to be calculated at each view angle. The rays of these interpolated projections are approximately coplanar with the segment. Thus, the interpolated projections are taken as the projections of the slice for 2D reconstruction of the image of the segment. It is convenient to denote $P_{i,j}(\phi)$ as $P_{klj}(\phi)$, to indicate that $P_{i,j}(\phi)$ are used as the projection data of the segment l in oblique slice k. That is, $$P_{klj}(\phi) = P_{i,j}(\phi) \quad (14)$$

with k=0, 1, ... $m_k$−1, l=1, 2, ..., $n_s$, and j=1, 2, ..., N. At view angle $\phi$, there are m oblique slices, each with $\Phi_k$ in the range of $\phi - \pi < \Phi_k \leq \phi$, measured by the detector array. Thus, there are $n_s$mN projection values $P_{klj}(\phi)$ to be interpolated for N channels in $n_s$ segments of m slices at each view angle.

Figure 15:
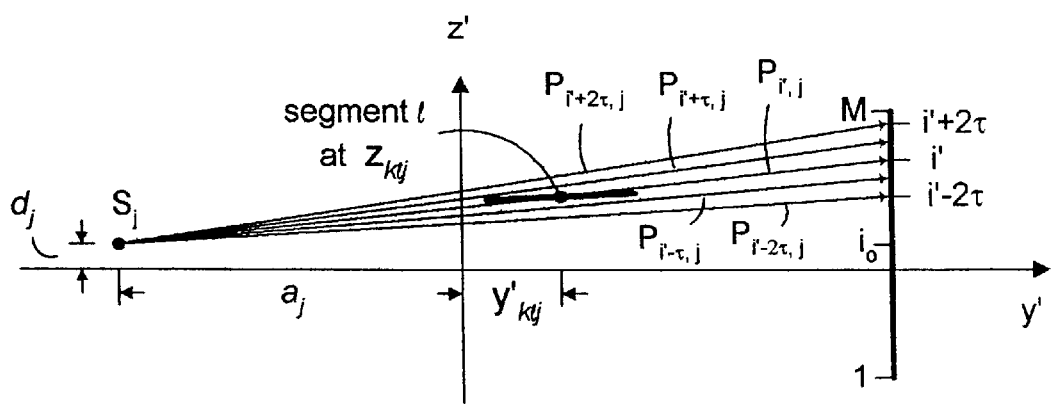
FIG. 15 schematically illustrates calculation of a projection value of a slice using a weighted sum of projection values of plural rays intersecting the slice, in accordance with the invention.

Although it is a good approximation to use $P_{i,j}(\phi)$ of the ray intersecting the segment middle line as the projection value $P_{klj}(\phi)$ of channel j in segment l of slice k as described above, other methods of generating $P_{klj}(\phi)$ are possible. One method is to compute $P_{klj}(\phi)$ as a weighted sum of the projection values of all the rays intersecting the segment at different y' locations as illustrated in FIG. 15.

For illustration purposes, it is assumed that the maximum number of rays to be used for the weighting is five, separated by an equivalent row number of $\tau$. The central ray intersects the focusing line of the oblique slice with projection value of $P_{i,j}(\phi)$. The weighted projection value for the channel j of segment l in slice k is calculated as $$P_{klj}(\phi) = w_0 P_{i,j}(\phi) + w_1 P_{i'+\tau,j}(\phi) + w_2 P_{i'-\tau,j}(\phi) + w_3 P_{i'+2\tau,j}(\phi) + w_4 P_{i'-2\tau,j}(\phi) \quad (15)$$

The weighting factors depend on the aberration angle $\epsilon_j$ and the relative z-position of the segment middle line with respect to the X-ray source position. They vary with the channel j and the view angle $\phi$. In general, we have $$w_0 + w_1 + w_2 + w_3 + w_4 = 1 \quad (16)$$

with $w_2 \cong w_1$, $w_4 \cong w_3$, and $w_0 \geq w_1 \geq w_3$. In this case, five projection values are interpolated or re-sampled from the collected projections $P_{ij}(\phi)$ for each channel. The weighting factors can be combined with the coefficients in the interpolation or re-sampling process, such that $P_{klj}(\phi)$ can be computed directly from the collected data $P_{ij}(\phi)$ as $$P_{klj}(\phi) = w_0 P_{qj}(\phi) = w_1 P_{q+\tau,j}(\phi) + w_2 P_{q-\tau,j}(\phi) + w_3 P_{q+2\tau,j}(\phi) + w_4 P_{q-2\tau,j}(\phi) \quad (17)$$

where q is the truncated integer of i' as described in Equation (12). The weighting factors here further depend on the difference between i' and q, and the relations $w_2 \cong w_1$, $w_4 \cong w_3$, and $w_0 \geq w_1 \geq w_3$ are not necessarily valid.

The example given here is a 5-term weighted projection value for the oblique slice. In practice, the spacing $\tau$ and the number of terms included for the weighting can be varied.

At each view angle, a total of $n_s$mN projection profiles are interpolated for the $n_s$ segments in m slices. Each projection profile contains N projection values $P_{klj}(\phi)$, with j=1, 2, ..., N for the segment l in slice k. The rays of these N projection values are separated by a non-equal spacing in the lateral dimension (the x' dimension). This is because the longitudinal fan j is at a nonlinear distance of r $\sin\gamma_j$=r $\sin((j-j_o)\delta)$ from the central longitudinal fan $j_o$, as shown in FIGS. 5 and 7.

For the subsequent convolution operation, it is required that these projection values be sampled at a constant lateral spacing. Therefore, the projection data $P_{klj}(\phi)$ are interpolated into equal lateral spacing at every view angle, like the parallel-beam projection data of a conventional single detector system. The lateral spacing at the central channel is r $\sin\delta \cong$ r $\delta$. If r $\delta$ is chosen as the constant spatial interval for all channels, the projection data $P_{klj}(\phi)$ will be interpolated into a constant spacing of r $\delta$. The interpolation is performed among the N channels of each segment in each slice. The total number of interpolations required is $n_s$mN at each view angle.

This equal lateral spacing interpolation can also be performed on the original data $P_{ij}(\phi)$ collected by each row of detectors, before they are used to calculate the projection values for each segment of the oblique slices. In that case, the parallel projections $P_{ij}(\phi)$ reordered from each row are interpolated into equal lateral spacing, for instance of r $\delta$. The total number of interpolations required is MN at each view angle, where M is the number of rows of detectors. With the N channel in equal spacing, the z position of the channel j in Equation (10) becomes $$z_{klj}(\phi) = z_o + k\, p/\pi - r\, \tan\alpha\, \sin(\phi - \Phi_k)_{(j-j_o)} \delta + y_{okl} \tan\alpha \cos^2(\phi - \Phi_k) - x_{okl} \tan\alpha\, \sin(\phi - \Phi_k) \quad (18)$$

Based on the equal spaced $P_{ij}(\phi)$ and Equation (18), the projection data $P_{klj}(\phi)$ interpolated to the segment l of oblique slice k will have equal lateral spacing of r $\delta$. In fact, it is preferred to perform the equal lateral spacing interpolation on the original data rather than on the projection profile of each segment, because the total number of interpolations in each view angle is reduced from $n_s$mN to MN. Because the number of rows of detectors M is on the order of the number of reconstructing slices m, the reduction factor is about $n_s$.

The N projection values of $P_{klj}(\phi)$ at equal spacing are then convoluted with a well-known convolution kernel for reconstruction of a 2D image. The convolution is performed at each view angle for each segment in each slice, in the same manner as in a conventional system with a single row of detectors. Let the convoluted projection value be $Q_{klj}(\phi)$. The convoluted projections $Q_{klj}(\phi)$ have equal spacing of r $\delta$ between adjacent channels. Whether this equal lateral spacing is performed before or after the generation of projections $P_l(\phi)$, the z position of the convoluted projection $Q_{klj}(\phi)$ is given by $z_{klj}(\phi)$ in Equation (18), where the N channels are at a constant lateral spacing of r $\delta$.

The constant lateral spacing r $\delta$ is measured on the xy plane and remains the same constant for all view angles. When these convoluted data are backprojected to a 2D matrix, the elements of the matrix are located at equally spaced (x,y) coordinates. The reconstructed image can be considered the image of the segment projected onto the xy-plane.

As described above, the projection profiles are optimally interpolated from the collected data for each segment. Consequently, the project profiles for one segment are slightly different from those for other segments. At the boundary of two adjacent segments, the image intensity in one segment is slightly different from that in the other segment. There is a slight discontinuity of the image intensity across the boundary. In order to avoid the discontinuity, it is preferred to reconstruct the segment slightly bigger than the intended area such that adjacent segments are slightly overlapped. Then in the overlapped region, the image intensity is gradually averaged from the two segments pixel by pixel, such that the image intensity is gradually changed over from one segment to the other.

Figure 16:
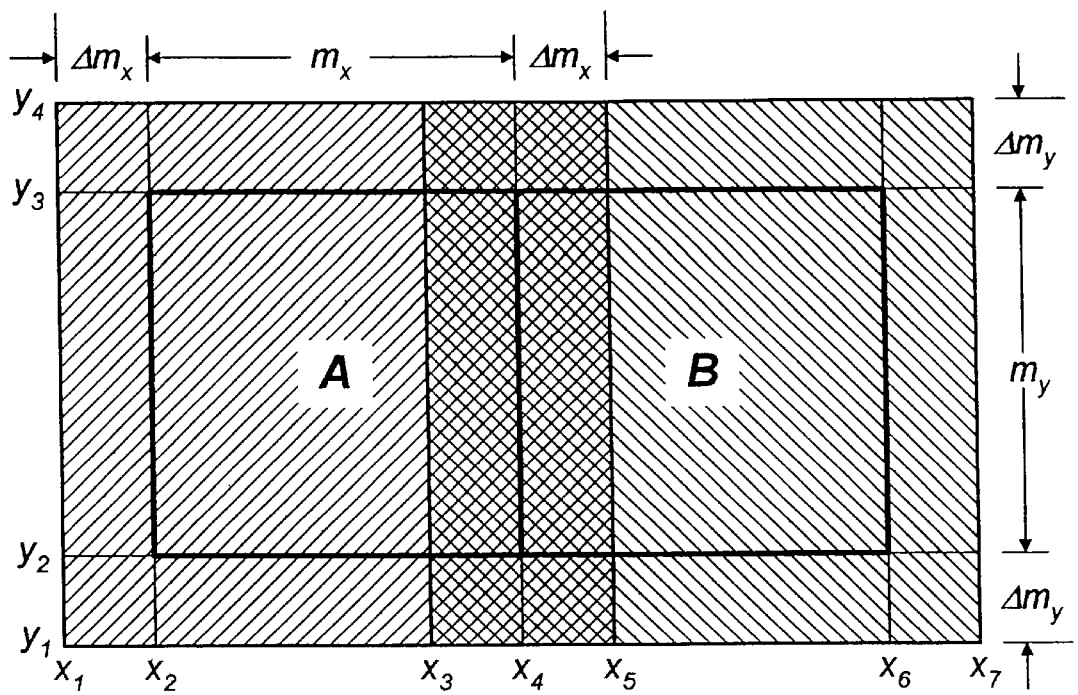
FIG. 16 contains a schematic diagram of overlapped regions of adjacent slice segments in accordance with the invention.

The imaging area of two overlapped segments along the x direction is shown in FIG. 16. The intended image area is $m_x$ by $m_y$ for each segment. Both segments are reconstructed to an area bigger than the intended image area with $n_x=m_x+2\Delta m_x$ in the x dimension and $n_y=m_y+2\Delta m_y$ in the y dimension. Segment A is located from $x_1$ to $x_5$ while segment B is located from $x_3$ to $x_7$. For segment A, the area between $x_4$ and $x_5$ is to be overlapped with segment B. If segment A is on the leftmost of the slice, the area between $x_1$ and $x_2$ can be omitted. Otherwise, it will be used to overlap with the segment on the left. The overlapped area between $x_6$ and $x_7$ in segment B is on the same assumption of having an adjacent segment there. So are the two overlapped areas in the y direction, from $y_1$ to $y_2$ and from $y_3$ to $y_4$.

Suppose the image intensities of segment A and B are $V_a(x, y)$ and $V_b(x, y)$. They are averaged pixel-by-pixel with weighting factors $W_a(x)$ and $W_b(x)$ for segment A and B, respectively. The averaged image intensity is given by $$V_{ab}(x, y)=W_a(x) V_a(x, y)+W_b(x) V_b(x, y) \quad (19)$$

for $x_1 \leq x \leq x_7$ and $y_1 \leq y \leq Y_4$. It can be considered a composite image ranging from $x_1$ to $x_7$ in the x direction and $y_1$ to $y_4$ in the y direction.

In one embodiment, the weighting factors have the following relations, $$W_a(x)+W_b(x)=1.0 \ W_a(x)=0 \text{ for } x>x_5 W_b(x)=0 \text{ for } x<x_3 \quad (20)$$

Figure 17:
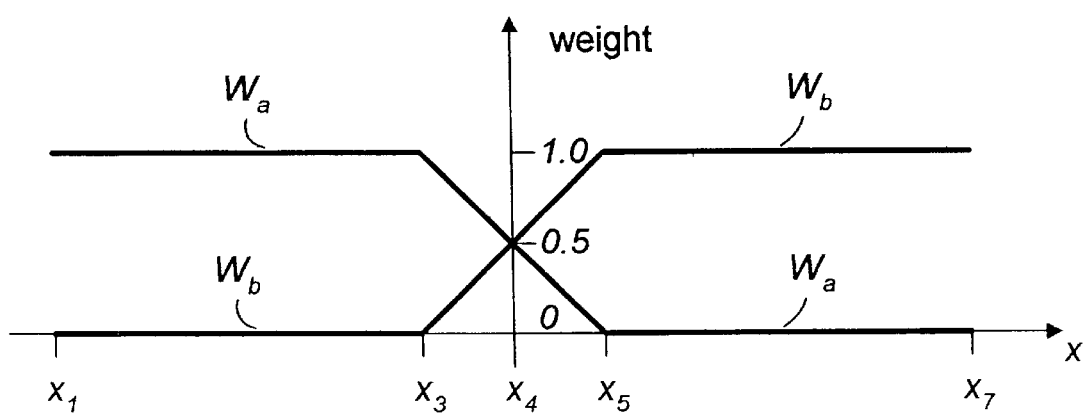
FIG. 17 contains a schematic plot which illustrates a linear weighting function for overlap areas in overlapped adjacent slice segments in accordance with the invention.

A preferred weighting function with linear weighting over the overlapped areas is plotted in FIG. 17. Other weighting functions, with nonlinear weighting over the overlapped areas can also be used.

The composite image is then averaged with adjacent segments along the x direction in the same manner as the averaging between segments A and B to become a larger composite image. When all segments along the x direction are processed, the composite image is averaged with adjacent composite images along the y direction, with weighting factors varied with the y coordinate in the same manner as in equations (19) and (20). Eventually, the composite image extends to the size of the whole slice and becomes the final image of the slice.

It does not matter whether the overlapping of segments is performed along the x- or y-direction first. However, for non-isometric partition of segments, such as the five segment partition in FIG. 12C, certain order of overlapping the segments into the composite image may be preferred. For example, in the five segment partition, it is preferred to perform overlapping of the four isometric segments first before overlapping with the central segment.

In general, the oblique slices are not parallel to each other. Although a stack of such oblique slices contains the full information of the volumetric image, it is generally preferred to store and display the volumetric image as a stack of normal slices. The location and orientation of the oblique slices are precisely known. Thus the image intensity of the normal slices can be interpolated from the reconstructed oblique slices along the z direction. The z coordinates of the oblique slices can be obtained by setting $\phi=0$ to Equation (7). At $\phi=0$, the rotating frame (x',y',z') coincides with the laboratory frame (x,y,z), and we have $$z=z_{kjo}+x \tan\alpha \sin \Phi_k+y \tan\alpha \cos \Phi_k \quad .(21)$$

Equation (21) indicates that at the same xy-location, the z coordinates of the oblique slices are not equally spaced. It can be time consuming to find the oblique slice nearest to the normal slice in the z direction. Therefore, it is preferred to pre-calculate the oblique slice number and the z coordinate of the oblique slice nearest to the normal slice at each pixel location, and store them in a lookup table for interpolating the image intensity of the normal slice.

Each normal slice has one lookup table for the interpolation. However, one lookup table can be shared for multiple slices. This is because $\sin\Phi_k$ and $\cos\Phi_k$ in Equation (21) are periodic functions of k with a period of 2m, as can be seen from Equation (4). When 2m oblique slices are grouped for the interpolation, the relative z locations with respect to the corresponding group of normal slices are the same for all groups. Thus, the total number of different lookup tables is no more than 2m. Furthermore, the lookup tables of the first m slices can be used to interpolate for the second m slices. In that case, the second m slices will be 180° rotated about the z-axis with respect to the first m slices. The 180° rotation of the images can be rectified. Therefore, the total number of lookup tables can be reduced to m, which is usually much smaller than total number of slices $m_k$.

Although it is preferred to select the oblique slices which are most coplanar with the rays for reconstruction, it is also possible to select other oblique slices. One particular set of slices for reconstruction is the normal slices, which are the special oblique slices with null oblique angle. In that case, each normal slice is divided into a number of segments as described above for an oblique slice. Each segment is then reconstructed independently and then averaged with other segments over the overlapped region to become the composite image of the normal slice.

Given the same number of segments, the reconstructed normal slice will not be as accurate the oblique slice. But under a small cone angle and an adequate number of segments, the images of normal slices may attain sufficient accuracy. Interpolation of the projection data for normal slices is simpler. More importantly, it avoids the process of rendering oblique slices into normal slices. Thus, under certain conditions, it may be preferred to select the normal slices for reconstruction.

It may also possible to select a set of oblique slices with a small oblique angle for reconstruction. The accuracy of images will be better than normal slices, because of non-zero oblique angle. Yet, the oblique angle may be small enough that the slices can be treated as normal slices for display. The purpose of this selection is to compromise the accuracy with the omission of rendering to normal slices.

Thus, in accordance with the invention, a new method is developed to generate accurate volumetric image for a cone beam scanner in a helical scan. A stack of slices is selected for reconstruction. Each slice is divided into multiple segments. The projection value of the segment at each channel is interpolated from the collected projection data at the projection path nearest to the segment. Each segment is reconstructed from a set of projection values optimally interpolated for that segment. The image of these multiple segments are then combined into a composite image of the slice.

In one embodiment, the slices are oriented at a certain oblique angle, such that the slice is most coplanar with the rays during the course of scanning. It is preferred to reorder the fan-beam projection data collected from each row of detectors into parallel-beam projection data as the basis for interpolating the projection values for each segment. It is also possible to interpolate the projection values for each segment directly from the original cone-beam data without the reordering of the projection data. In that case, a set of fan-beam projection values is optimally interpolated for each segment at each view angle. As in the reconstruction of a 2D image from a conventional CT system with a single row of detectors, the interpolated fan-beam projection data can be used to reconstruct the image of the segment or reordered to parallel-beam projection data for reconstructing that segment.

The number of computations in reconstructing an image is largely dominated by backprojection, which is proportional to the image size and the number of view angles in the projection data. By dividing each slice into overlapped segments, the backprojection time increases only slightly to account for the overlapped area. Convolution is the next most intensive computation in the reconstruction process, but it is far less than the backprojection. Since convolution is applied to the projection profile of each segment, the total computing time for convolution is proportional to the number of segments.

When a slice is divided into more segments, each segment will cover a smaller image area. The projection path of the interpolated projection values will be more consistent with the segment. Thus, the reconstructed image will be more accurate with more segments in a slice. On the other hand, it is desirable to keep the number of segments per slice as small as possible to minimize the convolution time. The preferred partitions are 4, 5, 9, and 16 segments per slice. At these number of segments per slice, the total reconstruction time will not be much greater than the prior method of reconstructing the whole slice without segmentation.

Although this invention has been described and illustrated using helical half-scan reconstruction, in which each slice is reconstructed from projection profiles over a view angle range of 180°, it is also applicable to helical full-scan reconstruction, where each slice is reconstructed from projection profiles over a view angle range of 360°. However, in this situation, the X-rays may not be more coplanar with an oblique slice than a normal slice over the 360° views. Thus, it may be preferred to select normal slices and partition each normal slice into multiple segments for helical full-scan reconstruction.

Similarly, the invention is also applicable to step-and-shoot "constant z-axis" scanning. In both half-scan and full-scan, the X-rays may not be more coplanar with an oblique slice than a normal slice. Again, it may be preferred to reconstruct normal slices for the constant z-axis scanning.

Although the embodiments of the CT scanner are described and shown as third generation types, wherein the detectors and x-ray source rotate about the longitudinal axis, other generation machines, such as fourth generation machines, wherein the x-ray source rotates about the longitudinal axis while the x-ray detectors remain fixed relative to the gantry frame, can also possibly be used.

While this invention has been particularly shown and described with references to preferred embodiments thereof, it will be understood by those skilled in the art that various changes in form and details may be made therein without departing from the spirit and scope of the invention as defined by the following claims.

What is claimed is:

1. A method of reconstructing image data for a region having a longitudinal axis, comprising:
   providing a radiation source and an array of detectors on opposed sides of the region, the radiation source emitting radiation toward the array of detectors, at least one of the radiation source and the array of detectors being rotatable about the longitudinal axis through a plurality of projection angles to scan the region to generate scan data for the region;
   defining at least one image slice for the region;
   partitioning the image slice into a plurality of image slice segments having different lateral locations within the image slice;
   generating image data for the plurality of image slice segments; and
   combining the image data for the plurality of image slice segments to generate image data for the image.

2. The method of claim 1 wherein each image slice segment is reconstructed from a set of projection values interpolated for the image slice segment.

3. The method of claim 1 wherein the image slice is an oblique image slice being oblique with respect to the longitudinal axis.

4. The method of claim 3 wherein an angle formed by the oblique image slice and the longitudinal axis is selected such that the oblique image slice is coplanar with the radiation source for at least one projection angle.

5. The method of claim 1 wherein at least two of the image slice segments overlap.

6. The method of claim 1 wherein the array of detectors is a two-dimensional array of detectors.

7. The method of claim 1 wherein the scan data are obtained by helical cone beam scanning of the region.

8. The method of claim 1 wherein the scan data are obtained by constant z-axis scanning of the region.

9. The method of claim 1 wherein half-scan reconstruction is applied to the scan data for the region.

10. The method of claim 1 wherein full-scan reconstruction is applied to the scan data for the region.

11. The method according to claim 1, wherein generating image data for the plurality of image slice segments includes generating image reconstruction data of the image for each segment, and combining the image data for the plurality of image slice segments includes concatenating the reconstructed data of the image for each segment.

12. An apparatus for reconstructing image data for a region having a longitudinal axis, comprising:
    a radiation source and an array of detectors on opposed sides of the region, the radiation source emitting radiation toward the array of detectors, at least one of the radiation source and the array of detectors being rotatable about the longitudinal axis through a plurality, of projection angles to scan the region to generate scan data for the region; and
    a processor for (i) defining at least one image slice for the region, (ii) partitioning the image slice into a plurality of image slice segments respectively having different lateral locations within the image slice, (iii) generating image data for the plurality of image slice segments, and (iv) combining the image data for the plurality of image slice segments to generate image data for the image slice.

13. The apparatus of claim 12 wherein the image slice is an oblique image slice being oblique with respect to the longitudinal axis.

14. The apparatus of claim 13 wherein an angle formed by the oblique image slice and the longitudinal axis is selected such that the oblique image slice is coplanar with the radiation source for at least one projection angle.

15. The apparatus of claim 12 wherein at least two of the image slice segments overlap.

16. The apparatus of claim 12 wherein the array of detectors is a two-dimensional array of detectors.

17. The apparatus of claim 12 wherein the scan data is obtained by helical cone beam scanning of the region.

18. The apparatus of claim 12 wherein the scan data are obtained by constant z-axis scanning of the region.

19. The apparatus of claim 12 wherein half-scan reconstruction is applied to the scan data for the region.

20. The apparatus of claim 12 wherein full-scan reconstruction is applied to the scan data for the region.

21. The apparatus according to claim 12, wherein a processor combines the image data for the plurality of image slice segments to generate image data for the image slice by concatenating the reconstructed data of the image for each image slice segment.

22. The apparatus of claim 12 wherein each image slice segment is reconstructed from a set of projection values interpolated for the image slice segment.

23. An apparatus for reconstructing image data for a region having a longitudinal axis, comprising:
    a radiation source and an array of detectors on opposed sides of the region, the radiation source emitting radiation toward the array of detectors, at least one of the radiation source and the array of detectors being rotatable about the longitudinal axis through a plurality of projection angles to scan the region to generate scan data for the region; and a processor for (i) defining at least one image slice for the region wherein the image slice is oblique with respect to the longitudinal axis, (ii) partitioning the image slice into a plurality of image slice segments, (iii) generating image data for the plurality of image slice segments, and (iv) combining the image data for the plurality of image slice segments to generate image data for the image slice.

24. The apparatus of claim 23, wherein an angle formed by the oblique image slice and the longitudinal axis is selected such that the oblique image slice is coplanar with the radiation source for at least one projection angle.

25. A method of reconstructing image data for a region having a longitudinal axis, comprising:

providing a radiation source and an array of detectors on opposed sides of the region, the radiation source emitting radiation toward the array of detectors, at least one of the radiation source and the array of detectors being rotatable about the longitudinal axis through a plurality of projection angles to scan the region to generate scan data for the region;

defining at least one image slice for the region oblique to the longitudinal axis;

partitioning the image slice into a plurality of image slice segments;

generating image data for the plurality of image slice segments;

combining the image data for the plurality of image slice segments to generate image data for the image slice.

26. The method of claim 25, wherein an angle formed by the oblique image slice and the longitudinal axis is selected such that the oblique image slice is coplanar with the radiation source for at least one projection angle.

* * * * *

UNITED STATES PATENT AND TRADEMARK OFFICE
CERTIFICATE OF CORRECTION

PATENT NO. : 6,256,366 B1　　　　　　　　　　　　　　　　　　　　　Page 1 of 1
DATED : July 3, 2001
INVENTOR(S) : Ching-Ming Lai It is certified that error appears in the above-identified patent and that said Letters Patent is hereby corrected as shown below:

<u>Column 20, claim 12,</u>
Line 27, after "plurality", delete ",".

Signed and Sealed this

Twenty-sixth Day of March, 2002

Attest:

JAMES E. ROGAN
Attesting Officer　　Director of the United States Patent and Trademark Office